United States Patent [19]

Fancher

[11] 4,058,535

[45] Nov. 15, 1977

[54] PROCESS FOR MANUFACTURING PHOSPHONO IMIDATES

[75] Inventor: Llewellyn W. Fancher, Orinda, Calif.

[73] Assignee: Stauffer Chemical Company, Westport, Conn.

[21] Appl. No.: 598,906

[22] Filed: July 24, 1975

Related U.S. Application Data

[63] Continuation-in-part of Ser. No. 468,333, May 9, 1974, abandoned, which is a continuation of Ser. No. 323,590, Jan. 15, 1973, abandoned.

[51] Int. Cl.$^2$ .................. C07D 209/02; C07D 277/38; A01N 9/36
[52] U.S. Cl. ......................... 260/326 E; 260/281 GP; 260/306.8 R; 260/326.5 A; 424/200
[58] Field of Search ..... 260/326 E, 281 GP, 326.5 A, 260/306.8 R

[56] References Cited

U.S. PATENT DOCUMENTS 3,450,713  6/1969  Tolkmith et al. ................. 260/326 E

*Primary Examiner*—Joseph Paul Brust
*Attorney, Agent, or Firm*—Daniel C. Block

[57] ABSTRACT

This invention relates to a process for manufacturing phosphono imidate compounds corresponding to the formula:

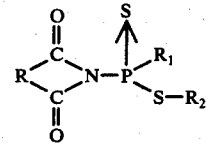

wherein R can be selected from alkylene having at least 2 carbon atoms, alkenylene having at least 2 carbon atoms, cycloalkylene, arylene, substituted arylene wherein the substituents can be halo or nitro; $R_1$ can be alkyl; $R_2$ can be selected from alkyl, alkenyl, alkynyl, cyano alkyl, aralkyl, alkanoyl alkyl, alkylmercapto alkyl, N-thiazolyl acetamido, phthalimido alkyl, arylthioalkyl, haloarylthioalkyl, thiocyanoalkyl and mixtures thereof.

2 Claims, No Drawings

PROCESS FOR MANUFACTURING PHOSPHONO IMIDATES

CROSS REFERENCE TO RELATED APPLICATIONS

This application is a continuation-in-part of application Ser. No. 468,333 filed May 9, 1974, now abandoned, which is a continuation of application Ser. No. 323,590 filed Jan. 15, 1973, now abandoned.

DESCRIPTION OF THE INVENTION

This invention is directed to a process for manufacturing a novel group of compounds which may generally be described as phosphono imidates which are active fungicides. The compounds of the present invention are represented by the generic formula:

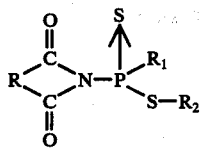

wherein R is selected from the group consisting of alkylene having 2–3 carbon atoms, alkenylene having 2–3 carbon atoms, cycloalkenylene, arylene, substituted arylene wherein the substituents are selected from halo and nitro; $R_1$ is alkyl having 1–6 carbon atoms; $R_2$ is selected from the group consisting of alkyl having 1–8 carbon atoms, alkenyl having 2–8 carbon atoms, alkynyl having 2–8 carbon atoms, cyano alkyl, aralykyl, alkanoyl alkyl, alkylmercapto alkyl, thiazolyl carbamyol alkyl, phthalimido alkyl, arylthioalkyl, haloaryl thioalkyl and thiocyanoalkyl.

The process for manufacturing the above defined compounds involves the reaction of the compound having the following formula:

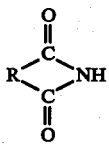 I wherein R is as defined above, with a compound having the following generic formula:

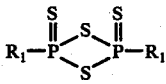 II wherein $R_1$ is as defined above;

The reaction product of the compounds identified in Formulas I and II is in fact a reactive mercaptan which is further reacted with an organo halide having the following general formula:

$R_2$—X    III wherein X is selected from chlorine, bromine and iodine, and $R_2$ is as defined above.

The reaction between the compound of Formula I and the compound of Formula II is carried out in the presence of a tertiary amine such as the trialkylamines wherein said alkyl moiety has from 1–8 carbon atoms and in the presence of a suitable solvent, such as benzene. The temperature of the overall reaction to form the end produce can range between 20° C. and 70° C. In general, the reaction scheme will be as follows:

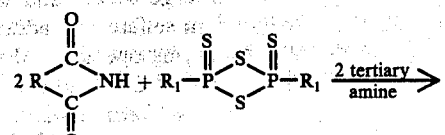

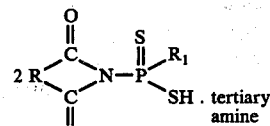

The reactive mercaptan formed by the above reaction is reacted with an organo halide to form the end product as follows:

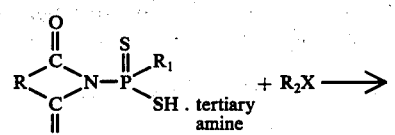

In the above reaction scheme, R, $R_1$, $R_2$ and X have been previously defined.

In order to illustrate the merits of the present invention, the following example is provided:

EXAMPLE 1

Into a 3-liter, three-necked, round-bottomed flask bearing a paddle stirrer and thermometer was placed 294 g. (2.0 M) of phthalimide and 1000 ml. of benzene, stirring was started and 222.2 g. (2.2 M) of triethylamine was added. To this slurry was added 322.4 g. (1.3 M) of ethylthionophosphine sulfide at 25° C. Since the reaction was exothermic, the temperature was held between 35–40° C. by occasional cooling in an ice bath. At this point, the mixture was found to be acidic and an additional 25 ml. of triethylamine was added to make the mixture slightly basic. The mixture was stirred at ambient temperature for 1 hour. To this mixture was added 343.2 g. (2.2 M) of ethyl iodide and the reaction mixture was heated with stirring at 65° C. for 1 hour. Then, an additional 600 ml. of benzene was added. The reaction product was washed with warm water. The mixture was then transferred warm to a 6 liter separatory funnel and approximately an equal volume of warm water (about 45° C.) was added. The separatory funnel was thoroughly shaken to mix contents and then filtered to remove a small amount of suspended solid. The solid remaining on the filter was washed with a small volume of warm benzene to remove any remaining product and the filtrate and washings were transferred to a 6 liter separatory funnel and the two layers allowed to separate completely. The aqueous bottom layer was drawn off and discarded. The benzene layer, containing the product, was washed with an equal volume of warm water by thoroughly shaking the funnel, the layers were allowed to separate and the bottom aqueous layer was removed and discarded. The benzene layer, containing the product, was placed in a large beaker and several grams of anhydrous magnesium sulfate was added and stirred by hand. During this drying operation, the temperature was maintained at 45°–50° C. to insure that the product remained in solution. The benzene-magnesium sulfate mixture was filtered warm and the filtrate was placed under water pump vacuum to remove the solvent. The solid obtained was slurried in cold ethyl ether, filtered and rinsed with cold ethyl ether again. The yield obtained, 492 g. (82% yield), m.p. 105°–106° C.

Other compounds were prepared in an analogous manner starting with the appropriate starting material as outlined above. The following is a table of compounds representative of those embodied by the present invention. Compound numbers have been assigned to them and are used for identification throughout the balance of the specification.

TABLE I

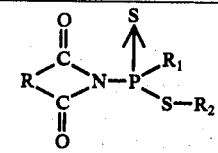

| Compound No. | R | $R_1$ | $R_2$ |
|---|---|---|---|
| 1 | phenyl | $C_2H_5$ | $CH_3$ |
| 2 | phenyl | $C_2H_5$ | $C_2H_5$ |
| 3 | phenyl | $C_2H_5$ | $CH_2CH=CH_2$ |
| 4 | phenyl | $C_2H_5$ | $CH_2C{\equiv}CH$ |
| 5 | phenyl | $C_2H_5$ | $CH(CH_3)(CH_2)_5CH_3$ |
| 6 | cyclohexenyl | $C_2H_5$ | $CH_3$ |
| 7 | cyclohexenyl | $C_2H_5$ | $CH_2C{\equiv}CH$ |
| 8 | cyclohexenyl | $C_2H_5$ | $CH_2CH=CH_2$ |
| 9 | $H_2C{-}/H_2C{-}$ | $C_2H_5$ | $CH_3$ |
| 10 | $HC{=}/HC{-}$ | $C_2H_5$ | $CH_3$ |

TABLE I-continued

| Compound No. | R | $R_1$ | $R_2$ |
|---|---|---|---|
| 11 | 2-nitrophenyl | $C_2H_5$ | $CH_3$ |
| 12 | 4-nitrophenyl | $C_2H_5$ | $CH_3$ |
| 13 | 2,3,4-trichlorophenyl | $C_2H_5$ | $CH_3$ |
| 14 | phenyl | $CH_3$ | $C_2H_5$ |
| 15 | 4-nitrophenyl | $C_2H_5$ | $C_2H_5$ |
| 16 | 2-nitrophenyl | $C_2H_5$ | $C_2H_5$ |
| 17 | phenyl | $C_2H_5$ | $n{-}C_3H_7$ |
| 18 | phenyl | $C_2H_5$ | $i{-}C_3H_7$ |
| 19 | phenyl | $C_2H_5$ | $n{-}C_4H_9$ |
| 20 | phenyl | $C_2H_5$ | $n{-}C_6H_{13}$ |
| 21 | phenyl | $C_2H_5$ | $n{-}C_7H_{15}$ |
| 22 | phenyl | $C_2H_5$ | $CH_2{-}phenyl$ |
| 23 | phenyl | $C_2H_5$ | $CH_2COCH_3$ |
| 24 | phenyl | $C_2H_5$ | $CH_2CN$ |

TABLE I-continued

[Structure: R-C(=O)-N(C(=O))-P(=S)(R1)(S-R2) ring]

| Compound No. | R | R1 | R2 |
|---|---|---|---|
| 25 | o-tolyl (ortho-methylphenyl) | C2H5 | CH2SCH3 |
| 26 | o-tolyl | C2H5 | CH2C(=O)-NH-(1,3-thiazol-2-yl) |
| 27 | o-tolyl | C2H5 | CH2N(phthalimido) |
| 28 | o-tolyl | C2H5 | CH2S-(2-chlorophenyl) |
| 29 | o-tolyl | C2H5 | CH2SCN |

FUNGICIDE TESTING PROCEDURES

A. Foliar Preventative Sprays

1. Bean Rust

The chemicals are dissolved in an appropriate solvent and diluted with water containing several drops of Tween-20, a wetting agent. Test concentration, ranging from 1000 ppm downward, are sprayed to runoff on the primary leaves of pinto beans (*Phaseolus vulgaris* L.). After the leaves are dried, they are inoculated with a water suspension of spores of the bean rust fungus (*Uromyces phaseoli* Arthur) and the plants are placed in an evironment of 100% humidity for 24 hours. The plants are then removed from the humidity chamber and held until disease pustules appear on the leaves. Effectiveness is recorded as percent reduction in number of pustules as compared to untreated inoculated plants.

2. Bean Powdery Mildew

Test chemicals are prepared and applied in the same manner as for the bean rust test. After the plants are dry, the leaves are dusted with spores of the powdery mildew fungus (*Erysiphe polygoni* De Candolle) and the plants are retained in the greenhouse until the fungal growth appears in the leaf surface. Effectiveness is recorded as percent of the leaf surface free of fungal growth as compared to untreated inoculated plants.

3. Tomato Early Blight

Test chemicals are prepared and applied in the same manner as the bean rust and powdery mildew tests except that 4-week old tomato (*Lycopersicon esculentum*) plants are utilized as the host plant. When the leaves are dry, they are inoculated with a water suspension of spores of the early blight fungus (*Alternaria solani* Ellis and Martin) and placed in an environment of 100% humidity for 48 hours. The plants are then removed from the humidity chamber and held until disease lesions appear on the leaves. Effectiveness is recorded as percent reduction in number of lesions as compared to untreated inoculated plants.

B. Foliar Eradicative Sprays

1. Bean Rust

Untreated bean plants are inoculated with spores of the bean rust fungus and placed in an environment with 100% humidity for 24 hours. They are then removed from the humidity chamber and held in the greenhouse for 2 days to allow the disease to become established. The test chemicals are then prepared and applied in the same manner as in the preventative spray test. Eradicative effectiveness is recorded as the percent reduction in number of pustules appearing in the leaves as compared to untreated inoculated plants.

2. Bean Powdery Mildew

Untreated pinto bean plants are dusted with spores of the powdery mildew fungus and maintained in the greenhouse until mycelial growth appears on the leaf surface. Test chemicals are then prepared and applied in the same manner as for the preventative spray test. Four days later the leaves are examined for inhibition of further mycelial growth. Eradicative effectiveness is recorded as the percentage of inhibition of viable, sporulating mycelium as compared to untreated inoculated plants.

C. Tube Systemic Test

1. Bean Rust

The chemicals are dissolved in an appropriate solvent and diluted with tap water to a series of descending concentrations beginning at 50 ppm. Sixty ml. of each concentration are placed in a test tube. A pinto bean plant is placed in each tube and supported with a piece of cotton so that only the roots and lower stem are in contact with the test solution. Forty-eight hours later the bean leaves are inoculated with a water suspension of spores of the bean rust fungus and placed in an environment with 100% humidity for 24 hours. The plants are then removed from the humidity chamber and maintained in the greenhouse until the disease pustules appear on the leaves. Effectiveness is recorded as the lowest concentration, in ppm, which will provide 50% reduction in pustule formation as compared to untreated, inoculated plants.

2. Bean Powdery Mildew

Test chemicals are prepared and applied in the same manner as for the bean rust systemic test. After two days the leaves are dusted with spores of the powdery mildew fungus and maintained in greenhouse until mycelial growth appears on the leaf surfaces. Effectiveness is recorded as the lowest concentration, in ppm, which will provide a 50% reduction in mycelial growth on the leaf surface as compared to untreated, inoculated plants.

TABLE II

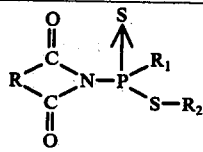

| Compound No. | Preventative ||||||||| Eradicative ||||||| Tube Systemic ||
| | Rust (ppm) ||| Mildew (ppm) ||| T.Blight (ppm) ||| Rust (ppm) ||| Mildew (ppm) ||| | |
| | 1000 | 500 | 100 | 1000 | 500 | 100 | 1000 | 500 | 100 | 1000 | 500 | 100 | 1000 | 500 | 100 | R | M |
|---|---|---|---|---|---|---|---|---|---|---|---|---|---|---|---|---|---|
| 1 | 50 | 25 | 0 | 90 | 75 | 0 | 100 | 90 | 50 | — | — | — | — | — | — | >50 | >50 |
| 2 | 100 | 95 | 50 | 98 | 75 | 25 | 100 | 100 | 100 | 50 | 0 | 0 | 75 | 50 | 25 | >50 | >50 |
| 3 | 90 | 75 | 25 | 100 | 75 | 25 | 100 | 100 | 100 | | | | | | | 50 | 50 |
| 4 | 50 | 25 | 0 | 75 | 50 | 0 | — | — | — | | | | | | | 50 | 50 |
| 5 | 0 | | | 0 | | | | | | | | | | | | | |
| 6 | 0 | | | 0 | | | | | | | | | | | | | |
| 7 | 0 | | | 0 | | | | | | | | | | | | | |
| 8 | 0 | | | 0 | | | | | | | | | | | | | |
| 9 | 0 | | | 0 | | | | | | | | | | | | | |
| 10 | 0 | | | 0 | | | | | | | | | | | | | |
| 11 | 25 | 0 | 0 | 0 | 0 | 0 | | | | | | | | | | | |
| 12 | 0 | 0 | 0 | 0 | 0 | 0 | | | | | | | | | | | |
| 13 | 50 | 25 | 0 | 0 | 0 | 0 | | | | | | | | | | | |
| 14 | 75 | 25 | 0 | 98 | 85 | 25 | | | | 0 | — | — | 25 | 20 | 0 | >50 | >50 |
| 15 | 25 | | | 0 | | | | | | | | | | | | | |
| 16 | 0 | | | 0 | | | | | | | | | | | | | |
| 17 | 75 | 50 | 25 | 100 | 95 | 50 | | | | | | | | | | | |
| 18 | 50 | | | 75 | 50 | 0 | | | | | | | | | | >50 | >50 |
| 19 | 50 | 25 | 0 | 80 | 75 | 0 | | | | | | | | | | >50 | >50 |
| 20 | 0 | | | 75 | 60 | 25 | | | | | | | | | | >50 | >50 |
| 21 | 50 | | | 50 | 25 | 0 | | | | | | | | | | >50 | |
| 22 | 50 | | | 0 | | | | | | | | | | | | >50 | |
| 23 | 0 | | | 0 | | | | | | | | | | | | | |
| 24 | 25 | | | 25 | | | | | | | | | | | | | |
| 25 | 0 | | | 25 | | | | | | | | | | | | | |
| 26 | 0 | | | 0 | | | | | | | | | | | | | |
| 27 | 0 | | | 25 | | | | | | | | | | | | | |
| 28 | 0 | | | 0 | | | | | | | | | | | | | |
| 29 | 99 | 95 | 80 | 0 | | | | | | | | | | | | | |

What is claimed is:

1. A process for manufacturing a compound having the formula:

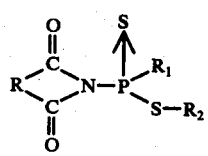

where R is selected from the group consisting of alkylene having 2-3 carbon atoms, alkenylene having 2-3 carbon atoms, cycloalkenylene, arylene, substituted arylene wherein the substituents are selected from halo and nitro; $R_1$ is alkyl having 1-6 carbon atoms; $R_2$ is selected from the group consisting of alkyl having 1-8 carbon atoms, alkenyl having 2-8 carbon atoms, alkynyl having 2-8 carbon atoms, cyano alkyl, aralkyl, alkanoyl alkyl, alkylmercapto alkyl, N-thiazoyl acetamido, phthalimido alkyl, arylthioalkyl, haloarylthioalkyl and thiocyanoalkyl; comprising the steps of:

a. reacting a compound having the formula:

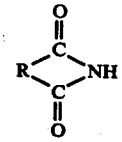

wherein R is as defined above; with a compound having the following generic formula:

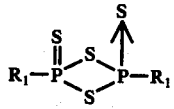

wherein $R_1$ is as defined above; said reaction being carried out in the presence of a tertiary amine;

b. reacting the product of a) with an organo halide with the formula $R_2-X$ wherein X is selected from chlorine, bromine and iodine, and $R_2$ is as defined above and in the presence of an inert solvent and at a reaction temperature of between 20° C. and 70° C. to form the end product.

2. The process of claim 1 wherein the solvent is benzene.

* * * * *